(12) United States Patent
Young et al.

(10) Patent No.: US 9,358,354 B2
(45) Date of Patent: Jun. 7, 2016

(54) APPARATUS AND METHOD FOR MONITORING AN AIRWAY DEVICE SUCH AS AN ENDOTRACHEAL TUBE

(71) Applicant: Indian Ocean Medical Inc., Mahe (SC)

(72) Inventors: Peter Young, King's Lynn (GB); Mario Zocca, Verona (IT)

(73) Assignee: Indian Ocean Medical, Inc., Mahe (SC)

( * ) Notice: Subject to any disclaimer, the term of this patent is extended or adjusted under 35 U.S.C. 154(b) by 0 days.

(21) Appl. No.: 13/621,983

(22) Filed: Sep. 18, 2012

(65) Prior Publication Data

US 2013/0014756 A1  Jan. 17, 2013

Related U.S. Application Data

(62) Division of application No. 12/678,368, filed as application No. PCT/GB2008/003151 on Sep. 16, 2008.

(30) Foreign Application Priority Data

Sep. 17, 2007 (GB) .................................. 0718086.2

(51) Int. Cl.
*A61M 16/00* (2006.01)
*A61M 16/04* (2006.01)
*G02B 6/44* (2006.01)

(52) U.S. Cl.
CPC ......... *A61M 16/0051* (2013.01); *A61M 16/044* (2013.01); *A61M 16/0409* (2014.02); *A61M 16/0434* (2013.01); *G02B 6/4459* (2013.01); *A61M 2016/0027* (2013.01)

(58) Field of Classification Search
CPC . A61M 16/00; A61M 16/04; A61M 16/0402; A61M 16/0434–16/0459; A61M 16/0465; A61M 16/0486

USPC ............ 128/200.24, 200.26, 207.14–207.17; 604/96.1, 103.03, 174, 505, 509, 513; 73/1.57, 1.79, 37, 37.5–37.6
See application file for complete search history.

(56) References Cited

U.S. PATENT DOCUMENTS 4,285,340 A * 8/1981 Gezari et al. ............. 128/205.24
4,630,606 A   12/1986 Weerda
(Continued)

FOREIGN PATENT DOCUMENTS

DE  9104637 U1  6/1991
EP  0578121 A1  1/1994
(Continued)

*Primary Examiner* — Jason Flick
*Assistant Examiner* — Ned T Heffner
(74) *Attorney, Agent, or Firm* — Ostrager Chong Flaherty & Broitman P.C.

(57) ABSTRACT

An airway device (14), that is used to maintain a clear airway in a patient, e.g. for artificial ventilation during surgery, comprises an inflatable cuff (26), which is inflated when in position in a patient's airway (24). The inflated cuff (26) provides a seal to maintain the device (14) in position in a patient's airway (24), and to prevent leakage of infected oropharangeal secretions into the patient's lungs. A method and apparatus (10) for monitoring and controlling the pressure in the inflatable cuff (26) is described, which, in one embodiment, controls the pressure about a setpoint pressure, whilst preventing loss of sealing pressure during a patient's respiratory cycle. In other embodiments, the method and apparatus monitors for: leaks in the pressure system of the device (14) that includes the cuff (26); blockage in the pressure system, and/or malpositioning of the airway device (14) during use.

10 Claims, 10 Drawing Sheets

(56) References Cited

U.S. PATENT DOCUMENTS

| | | | |
|---|---|---|---|
| 4,924,862 A | | 5/1990 | Levinson |
| 5,235,973 A | * | 8/1993 | Levinson ................. 128/207.15 |
| 5,255,670 A | * | 10/1993 | Lomholt ................. 128/200.24 |
| 5,361,753 A | | 11/1994 | Pothmann |
| 2003/0172925 A1 | | 9/2003 | Zocca |

FOREIGN PATENT DOCUMENTS

| | | |
|---|---|---|
| WO | 9933508 A1 | 7/1999 |
| WO | 0204058 A2 | 1/2002 |

\* cited by examiner

APPARATUS AND METHOD FOR MONITORING AN AIRWAY DEVICE SUCH AS AN ENDOTRACHEAL TUBE

RELATED APPLICATIONS

This application is a divisional application of, and claims priority under 35 U.S.C. §120 to, U.S. patent application Ser. No. 12/678,368.

TECHNICAL FIELD

The present invention relates to the monitoring of an airway device, such as an endotracheal tube or other pharyngeal/laryngeal device for maintaining an open airway in an animal or human patient.

BACKGROUND

An endotracheal tube, or similar airway device, is used to maintain a clear airway in a patient, e.g. for artificial ventilation during surgery. Typically, the device includes an inflatable cuff, which is inflated when in position in a patient's airway. The inflated cuff forms a seal, between the airway device and the tissues surrounding the airway, to thereby maintain the device in position in a patient's airway, and to prevent leakage of infected oropharyngeal secretions into the patient's lungs.

WO-A-99/33508 describes an apparatus that includes a monitoring system for monitoring pressure in the cuff of a laryngeal mask airway device, and for maintaining the inflated cuff at a preset pressure, within narrow tolerances. In particular, the apparatus periodically measures the pressure within a closed system incorporating the inflated cuff and compares the measured pressure with a preset pressure, to determine a difference and its polarity. The apparatus then controls the pressure within the closed system to reduce the difference to zero. The disclosure of WO-A-99/33508 is incorporated herein, by reference.

SUMMARY

The present invention seeks to provide improvements over the existing apparatus described in WO-A-99/33508.

According to a first aspect, the present invention provides a method for monitoring a pressure of an inflatable seal of an airway device, the method comprising: periodically receiving a pressure value indicative of the pressure of the inflatable seal; comparing the received pressure value with a preselected, desired pressure value, and, if a difference between the received pressure value and the preselected pressure value is greater than a predefined tolerance, changing the pressure of the inflatable seal, to reduce the difference, characterised in that the step of changing the pressure is carried out at a rate dependent upon a difference between the received pressure value and the desired pressure value.

In prior art techniques, it is typical to respond quickly to correct pressure deviations from a set point. However, cyclic pressure changes in the inflatable seal occur as a result of intra-thoracic and intra-tracheal pressure from the patient's airway during the breathing cycle. In certain circumstances, responding instantaneously to correct pressure deviations resulting from normal cyclic changes may reduce the inflation pressure to below a minimum required to create a seal with the airway. This may lead to leakage of secretions past the seal into the patient's lungs, and increase the risk that the airway device may be dislodged.

Accordingly, the present invention minimises this problem, by controlling the rate at which the pressure is changed in response to a detected deviation or change in pressure from the desired pressure. Thus, instead of making an instantaneous change in pressure to correct for the deviation, the pressure is adjusted at a rate dependent upon the deviation of the measured pressure value from the desired pressure value. The rate of adjustment may be further limited by a threshold value. By controlling the rate of pressure adjustment, the time taken to correct for the deviation from the desired value is delayed. Typically, the rate of adjustment produces a delay for a period that corresponds to, or is greater than, a normal time period for inspiration or expiration, which represents the greatest deviation in pressure associated with the breathing cycle.

In one embodiment, the rate of change of pressure is dependent on the square of the difference between the measured pressure value and the desired value.

For example, in an embodiment in which a piston is utilised to change the volume, and hence the pressure, in a closed volume system, the piston is moved at a rate N that is defined by the equation:

$$N = \frac{((P_1 - S)^2 * S)}{(R)}$$

Where: $P_1$ is the actual measured pressure
S is the set point or desired pressure
\* is the multiplier operation
R is a regulation constant In one embodiment, the rate N is a speed that corresponds to the number of steps per second moved by a stepper motor driving the piston.

The rate N may be subject to a predetermined maximum threshold speed. Thus, if the calculated rate N is greater that the threshold, the piston is controlled to move at the threshold rate.

Typically, if the measured pressure is higher than the set-point/desired pressure, the motor drives the piston backward at rate N in order to reduce pressure, and if the measured pressure is lower than set-point motor drives the piston forward at rate N in order to increase pressure.

In one embodiment, the measured pressure value is received at periodic time intervals, for example time intervals in the range of 0.1 to 2.5 seconds, and the rate of change of volume, and thus pressure, recalculated and adjusted. In one embodiment, the rate is recalculated every 0.5 seconds.

According to the second aspect, the present invention provides a method for detecting a change in position of an airway device with an inflatable seal, the method comprising: comparing a received pressure value indicative of a pressure of the inflatable seal with a predefined pressure value to determine a difference, and, if the difference is greater than a predetermined amount for a predetermined time period, indicating a detected change in position of the airway device.

A change in position of an airway device, such as an endotracheal tube, may arise during medical or surgical procedures and may be hidden (i.e. not detectable by those monitoring the patient). Such changes may lead to extubation, whereby the endotracheal tube cuff is unintentionally withdrawn into the patient's larynx or airway above. However, since the laryngeal volume is normally considerably greater than that of the trachea, it is possible to detect such hidden extubation, in accordance with the present invention, by monitoring for a change, in particular a substantial drop, in pressure.

In one embodiment, the predefined pressure value is a previous pressure value that is within predefined tolerances of a preselected, desired pressure value. In another embodiment, the predefined pressure value is a preselected, desired pressure value.

In one embodiment, the predetermined amount is a proportion of a predefined pressure value. In one embodiment, the predetermined amount is 20% of the predefined pressure value, so that a change in position is detected if the received pressure value is below 80% of the predefined pressure value for a predetermined time period.

The predetermined time is typically in the region of 15 seconds to 2 minutes, and in one embodiment is 60 seconds.

In one embodiment, the method comprises: receiving a first pressure value indicative of a pressure of the inflatable seal, the first pressure value within predefined tolerances of a preselected, desired pressure value; thereafter, periodically receiving further pressure values at predetermined time intervals; comparing each received further pressure value with the first pressure value to determine a difference; if the difference is greater than a predetermined amount, starting a timer for a predetermined time period, and, if the further, periodically received further pressure values are not within the predefined tolerances of the preselected pressure value before the timer has expired, indicating a detected change in position of the airway device.

It will be appreciated that in other embodiments, the difference between the received pressure value and the predefined pressure value need not be calculated. Rather, the received pressure value may be compared with a minimum value corresponding to predetermined proportion of the predefined pressure value (e.g. 80% of the predefined pressure value), and if the received value is less that the minimum value, the timer started.

According to a third aspect, the present invention provides a method for detecting a leak of fluid from an inflatable airway device, the method comprising: receiving a pressure value for the inflatable airway device; calculating a statistical average of values calculated using the received pressure value and a predetermined number of previously received pressure values, and, if the statistical average exceeds a threshold average, indicating a leak of fluid from the airway device.

In one embodiment, the values calculated using the received and previously received pressure values are values that represent a rate of change in volume or pressure of fluid in the inflatable airway device. Preferably, the rate of change in volume or pressure corresponds to a change to increase the pressure in the inflatable airway device.

A leak of fluid used to inflate and pressurise a seal of an airway device can adversely affect the proper functioning of the airway device. It is therefore important to monitor for and detect leaks of inflation fluid, to enable these to be manually corrected, wherever possible. In accordance with the present invention, this can be achieved by monitoring the pressure of the inflatable seal.

During use of an airway device, it is possible that a leak may be present in the airway device. Such a leak may be caused by perforation during surgery, or may be a slow leak from connections in the pressure system. According to the present invention, if a leak occurs whilst the airway device in use, it can be detected by calculating a statistical average of a number of values, that are each dependent on a corresponding number of previously received pressure values, and comparing it with a threshold statistical average. For example, the value may be a calculated rate of change of volume or pressure, as determined in accordance with the first aspect of the present invention. If the average is above a threshold, this indicates significant changes have been necessary over an immediately preceding time interval, to increase pressure to the desired pressure, thus signifying a possible leak of fluid.

According to a fourth aspect, the present invention provides a method for detecting a leak of fluid from an inflatable airway device, the method comprising: periodically receiving a pressure value for the inflatable airway device; comparing the received pressure value with a predetermined, minimum pressure value, and if the received pressure value is less than the predetermined minimum pressure value, indicating a leak of fluid from the airway device.

In one embodiment, the predefined minimum pressure value is a predetermined proportion of a preselected, desired pressure value, for example 50% of the preselected pressure value.

When an airway device is first introduced into a patient, and inflated, pressure adjustments are made until a desired pressure value is achieved. Thereafter, the pressure value is periodically monitored to detect a sudden drop in pressure. In accordance with the present invention, if the measured pressure value is less than a predetermined proportion of the preselected pressure value, for example 50%, this signifies a sudden loss of fluid from the pressure system, and thus a leak is detected.

According to a fifth aspect, the present invention provides a method for detecting a blockage in a pressure system of an inflatable airway device, the method comprising: receiving a pressure value for the inflatable airway device and calculating a current activity, and, if the current activity is below a threshold for activity for a predetermined time period, indicating a blockage in the pressure system of the airway device.

In one embodiment, activity is calculated by comparing the received pressure value with a desired or average pressure to calculate a difference. Activity is then determined by as a statistical average of the difference and a predetermined number of differences calculated using previously received pressure values.

Solid material can be introduced into a closed volume pressure system of an airway device in certain circumstances. This can lead to a blockage, adversely affecting the proper functioning of the pressure monitoring system. When a blockage occurs, the pressure becomes substantially static, and normal cyclic changes of pressure, associated with ventilation, are not detected. The present invention detects a blockage in the pressure system of an airway device if the average value of deviations in pressure from a desired value, over a predetermined time period, is below a threshold. The threshold is typically less that an average of deviations over the predetermined time period that would be expected to arise as a result of the breathing cycle.

In accordance with a sixth aspect, the present invention provides a computer readable medium comprising program instructions which, when executed, perform the method of any one or more of the first, second, third, fourth and fifth aspects of the present invention.

In accordance with the seventh aspect, the present invention provides an apparatus comprising processor means, configured for carrying out the method of any one or more of the first, second, third, fourth and fifth aspects of the present invention.

As the skilled person with appreciate, each of the methods of the first, second, third, fourth and fifth aspects of the present invention can be utilised in combination, and is typically implemented in the form of software, executed on a computer processor. It will be appreciated that the methods of the present invention may equally be implemented in the form of hardware.

Other desired and optional features and advantages of the present invention will be apparent from the following description and accompanying claims.

BRIEF DESCRIPTION OF THE DRAWINGS

Embodiments of the present invention will now be described, by way of example, with reference to the accompanying drawings in which.

DESCRIPTION OF PREFERRED EMBODIMENTS

In the following description of embodiments of the present invention, the described monitoring and control apparatus includes a closed volume pressure system which includes an inflatable seal of an airway device. In the described embodiments, an endotracheal tube is described, by way of example of a suitable airway device. The skilled person will appreciate that at least some of the embodiments may be implemented in conjunction with other forms of airway device, such as a laryngeal mask airway device. In addition, whilst the use of a closed volume system is advantageous, at least some of the embodiments may be used in conjunction with other systems for monitoring and controlling the pressure of an inflatable seal of an airway device.

Figure 1:
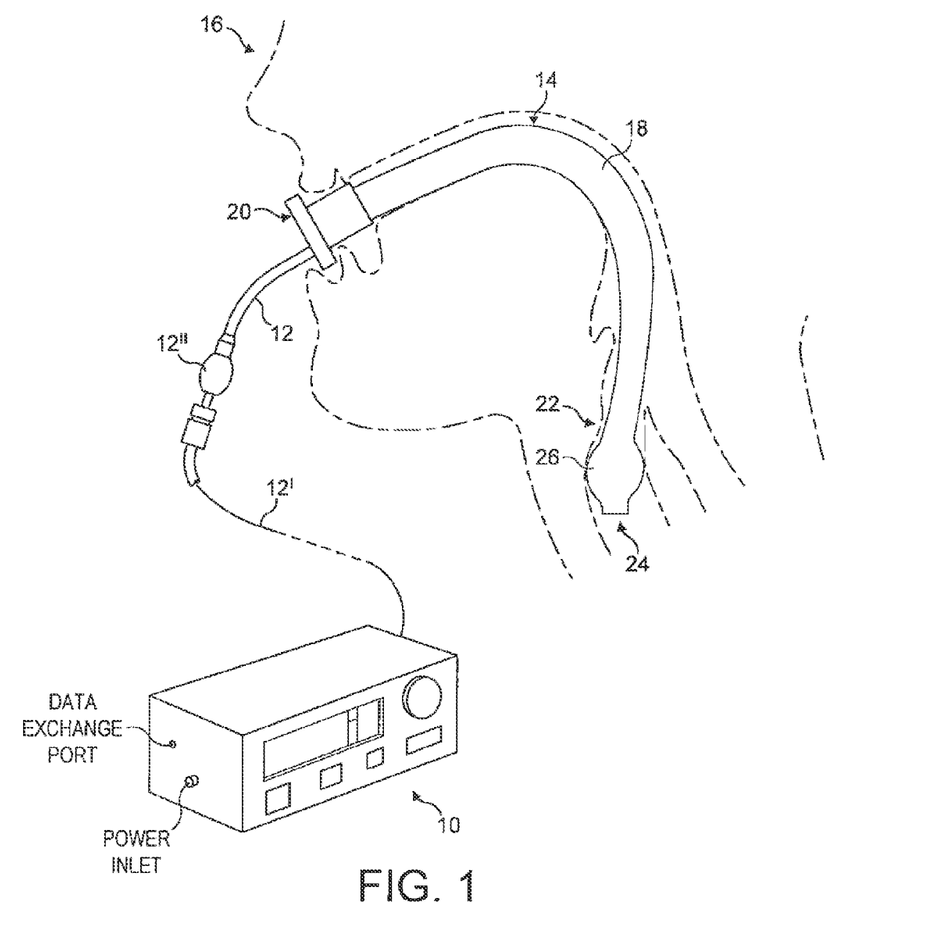
FIG. 1 is a schematic, perspective view of an apparatus in accordance with an embodiment of the present invention, coupled to an airway device in position in a patient.

FIG. 1 shows a pressure control and monitoring apparatus 10, according to an embodiment of the present invention, connected to a flexible inflation/deflation air supply line 12 of an airway device 14 positioned for use in maintaining a clear airway in a patient 16.

The airway device 14 comprises an airway tube 18 with a proximal end 20 for connection to an external ventilating or anaesthetizing supply to the patient's lungs and a distal end 22 for insertion into the trachea 24 of a human or animal patient. As shown in FIG. 1, the distal end 22 of tube 18 is peripherally surrounded by an inflatable/deflatable ring or cuff 26 of resiliently flexible material. The cuff 26, which is formed from a flexible, resiliently deformable material, is shown in inflated condition in FIG. 1 and forms a seal between the airway device 14 and the surrounding body structure of the patient 16, i.e. the wall of the trachea 24.

The structure of airway device 14 is conventional, and well known in the art. Examples of a suitable endotracheal tube include the Portex Soft Seal tracheal tube and the LoTrach tracheostomy tube.

Typically, the cuff 26 of the airway device 14 is manually inflated, once positioned in a patient, as shown in FIG. 1. Thereafter, the pressure monitoring and control system 10 can be utilized by connecting the airway device 14 to inflation/deflation air supply line 12 of apparatus 10.

Figure 2:
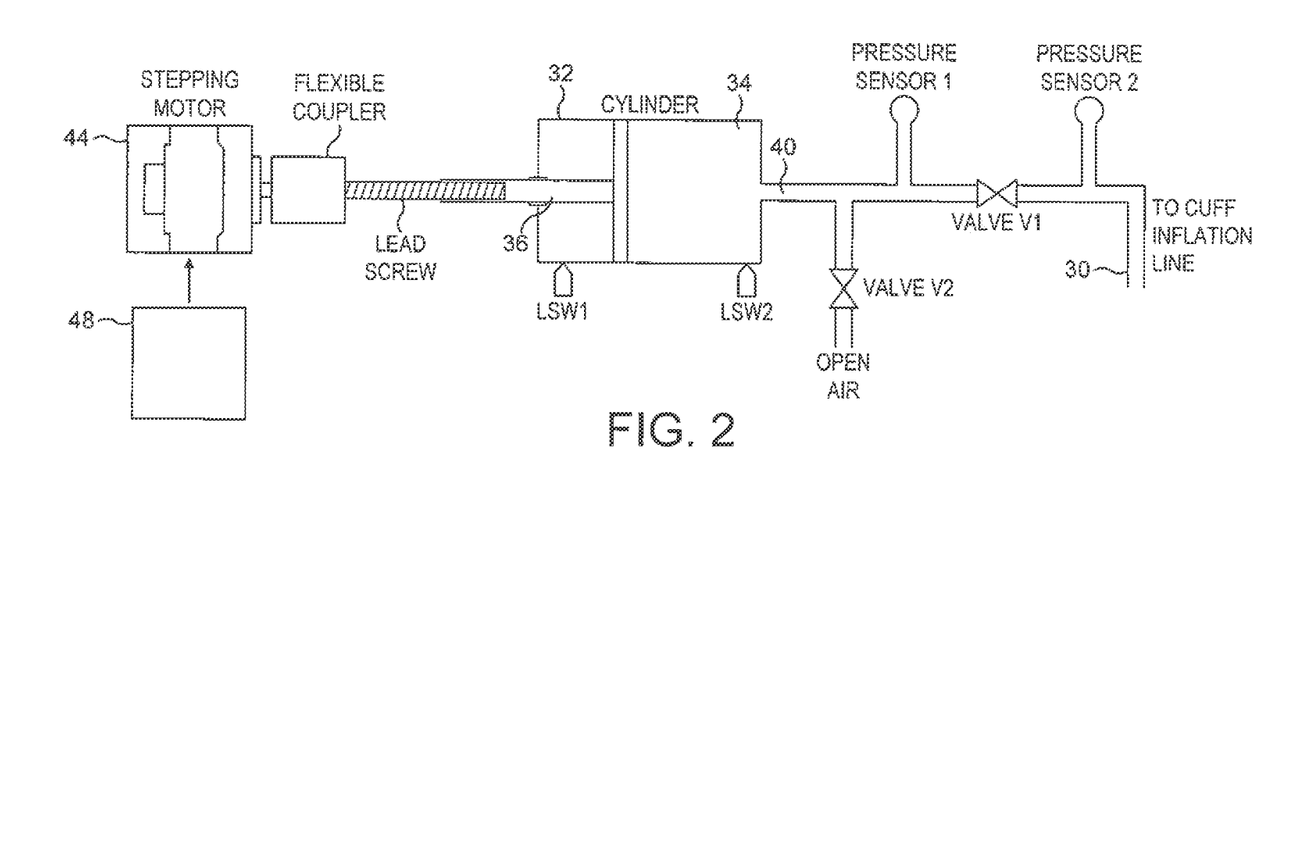
FIG. 2 is a schematic block diagram illustrating the apparatus of FIG. 1.

FIG. 2 shows schematically components of the pressure monitoring and control system 10, which comprises an air-control port 30 adapted for detachable connection to the inflation/deflation air supply line 12. An elongate flexible connection or extension line 12' (FIG. 1) is detachably connectable to control port 30 at one end, and, at the other end, is connectable to the connector end of a check-valve 12". In this way, air lines 12, 12' provide a continuously open passage of a pressure system in communication with inflatable cuff 26 of the airway device 14 and an air displacement mechanism within the housing of apparatus 10, as described below.

Air-displacement mechanism comprises a syringe in the form of a body 32 of low-friction material such as PTFE with a cylindrical bore 34 having an open (or tail) end for coaction with a piston 36. Body 32 is fixed to a frame and extends longitudinally to a closed (or head) end having a port connection 40 to a direct line to air control port 30. In this direct line, a first normally closed solenoid valve V1 must be actuated to open condition if inflation air is to pass in either direction between cylinder 34 and the inflatable/deflatable cuff 26 of the airway device 14.

Figure 3:
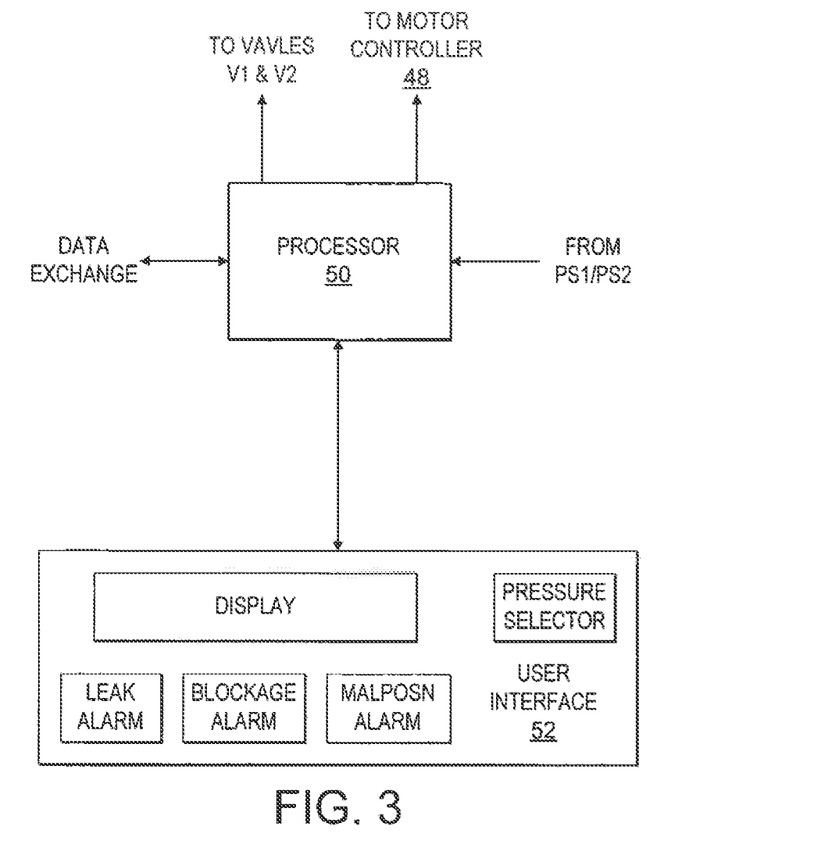
FIG. 3 is a block diagram illustrating the control and monitoring apparatus of FIG. 1, which implements the method of embodiments of the present invention.

Piston 36 is rigidly mounted to a support and guide means (not shown) to enable the piston 36 to be driven longitudinally through the cylindrical bore 34, with precise alignment with the central axis of the bore. Piston 36 is driven by step motor 44, which has a precise directional control via variance of the relative excitation of each of four input terminals under the control of motor controller and driver means 48, as shown in FIG. 3. Motor controller and driver means 48 operates in response to commands from a processor 50 (not shown) to change the pressure in the cuff 26, by altering the volume of the closed volume system formed between syringe body 32 and cuff 26 of the airway device 14. In particular, adjustments for cuff pressure deviation are made by increments of displacement of air in the closed volume system, each increment (corresponding to a step of motor 44) moving, for example, approximately 0.0005 ml. This enables pressure adjustments with a high degree of accuracy.

The apparatus of the present invention measures the instantaneous pressure in the closed volume system. In particular, apparatus 10 includes first and second pressure sensors PS1, PS2, which are connected to redundantly monitor air pressure in the line between cylinder-outlet port 40 and the normally closed first solenoid valve V1. Thus, except in the case of error, first and second sensors PS1, PS2 should produce the same pressure reading A second normally closed solenoid valve V2 is shown connected to the air line between cylinder port 40 and the first solenoid valve V1. When actuated to open condition, valve V2 establishes a path from its open-air end to the air line from cylinder port 40 to the first solenoid valve, so that, with valve V1 in its closed unactuated condition and with valve V2 actuated to its open condition, a right to-left (backward) displacement of piston 36 in cylindrical bore 34 will induce an inflow of fresh (ambient) air into the closed volume pressure system. Similarly, with the two valves V1 and V2 in the same condition (of V2 actuated and of V1 in its normally closed condition), a left to-right (forward) displacement of piston 36 in bore 34 will discharge excess air or gas from the system.

Also, and analogously, with valve V2 in its normally closed condition and with valve V1 actuated to its open condition, a right-to-left (backward) displacement of piston 36 will draw inflation air from (and thus deflate) cuff 26 of the airway device 14, and for the same conditions, of valve V2 unactuated and of valve V1 actuated, a left-to-right (forward) displacement of piston 36 will supply inflation air to inflatable cuff 26 of the airway device, thereby increasing pressure.

Control signals necessary for actuation of valves V1 and V2 are provided by program-sequencing signals from the processor 50 of the apparatus 10 (as shown in FIG. 3 described below) in accordance with conventional techniques.

FIG. 3 shows logic components of the apparatus 10 for monitoring and controlling the inflation pressure of the cuff 26 of an airway device 14, for example, as shown in FIG. 1. The apparatus 10 comprises a processor 50 that receives input signals from the first and second pressure sensors PS1, PS2 and provides control signals to the step motor controller and driver 48, and the valves V1 and V2, and outputs signals to a user interface 52 to provide information such as the selected and measured pressure values, and to provide alarm indications, in accordance with one or more methods of embodiments of the present invention.

As the skilled person will appreciate, processor 50 may comprise a programmable microprocessor, microcontroller or the like, that executes program instructions to perform methods in accordance with embodiments of the present invention. Alternatively, parts of the functionality of processor 50 may be conveniently implemented in hardware, for example as described in WO-A-99/33508.

Apparatus 10 operates in a similar manner to the apparatus described in WO-A-99/33508. In particular, the System Start Up, Failsafe and Normal System Control operations are analogous to those described in WO-A-99/33508, and so will not be described in detail herein.

As described above, apparatus 10 monitors and regulates the inflation pressure of the airway device cuff 26. A patient is typically mechanically ventilated, i.e., the patient's ventilation is the result of positive pressure being exerted through airway tube 18, also referred to as intermittent positive-pressure ventilation or "IPPV". As a result, apparatus 10 measures oscillations in pressure about a midline pressure value. These oscillations correspond to the respiratory cycle, which is about twelve cycles per minute for a typical anaesthetized adult patient. Thus, respiratory flow through airway tube 14, whether spontaneous or by IPPV, will have the effect of causing the cuff 26 to undergo regular cycles of compression/expansion. This results in cyclic changes in pressure, due to the change in volume of the resiliently deformable cuff 26 caused by this compression/expansion.

Whilst the known system of WO-A-99/33508 does not perform pressure adjustments when a pressure difference is detected within a tolerance band that is centred at a setpoint (corresponding to the midline), to allow for the above described oscillations, the system responds immediately when a pressure difference outside these tolerances is detected. In particular, the system controls piston 36 so that it is immediately displaced an appropriate distance to correct for the measured deviation from the setpoint. However, this may cause the pressure in the cuff 26 to overshoot or undershoot the tolerance band around the setpoint due to changes caused by the respiratory cycle. As a result, the cuff pressure may drop below the minimum pressure required to create a seal, risking leakage of secretions and possible movement of the airway device, or may exceed a maximum pressure, risking possible injury to the patient.

Figure 4:
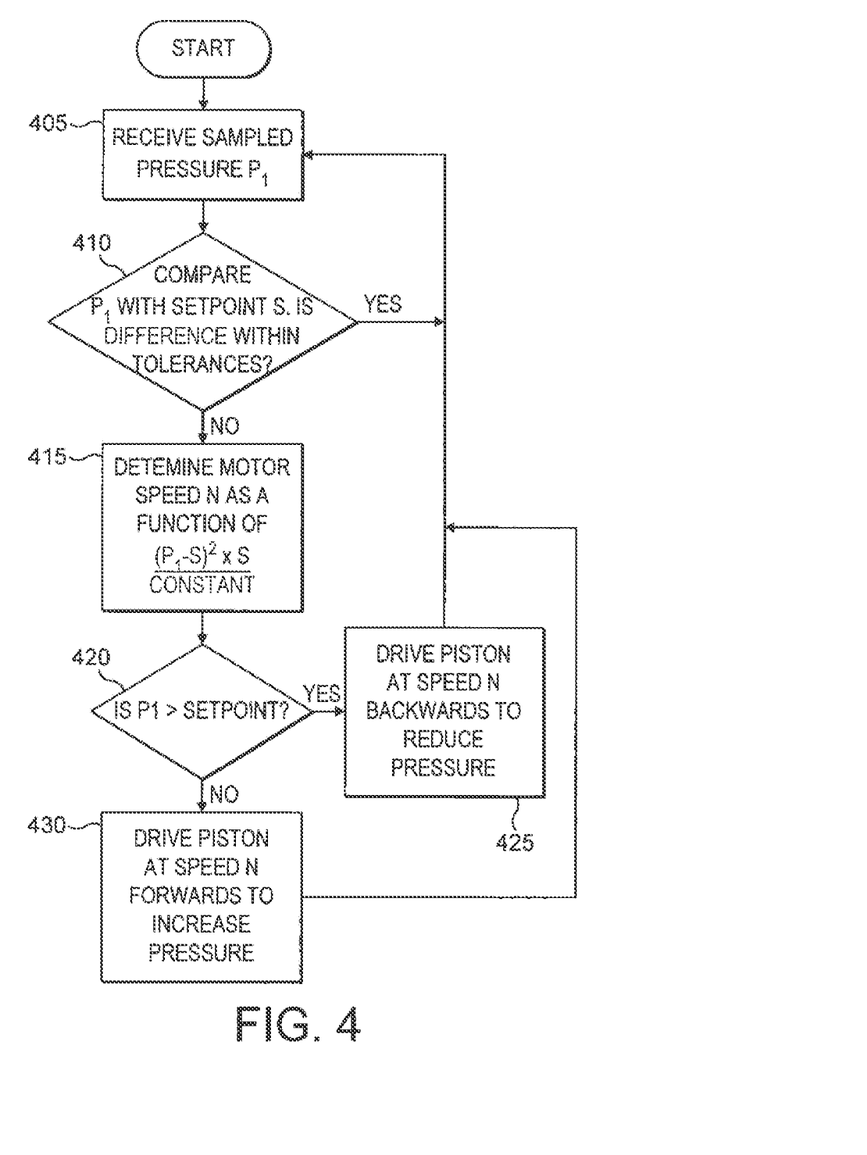
FIG. 4 is a flow diagram illustrating the method steps performed for controlling pressure in an airway device, in accordance with a first embodiment of the present invention.

FIG. 4 is a flow diagram illustrating the steps performed by processor 50 implementing a method for adjusting the pressure of the closed volume system of the above-described device in accordance with a first embodiment of the present invention. The method corrects for deviations from a desired pressure, outside a predetermined tolerance band, whilst ensuring that the inflation pressure does not drop below a minimum required to create a seal with the airway. In particular, the method controls the rate at which pressure is changed in response to detected pressure deviations, to allow for deviations resulting from normal pressure changes associated with the breathing cycle of the patient.

The method starts after the pressure $P_1$ of the inflatable cuff 26 of the airway device 14 has been established within a predefined tolerance band centred at a preselected set point pressure value, in accordance with the conventional System Start-Up procedure. As the skilled person will appreciate, the setpoint is chosen by the operator from a number of possible midline pressure values which are typically used for different patients such as children, male and female adults. In this embodiment, cuff pressures values of 20, 30, 50 and 50 mmHg may be selected by the operator, although the apparatus may provide for other suitable pressure values to be selected.

Accordingly, at step 405, the method receives a measured pressure value from one of the first and second pressure sensors PS1, PS2 of apparatus 10 corresponding to a pressure $P_1$ of the inflatable cuff. At step 410, the method compares the measured pressure value $P_1$ with the selected setpoint value S, to determine a difference $(P_1-S)$, and considers whether the difference is within the predefined tolerance band (e.g. S+/− 0.5 mmH2O (mmHg)). If, on the one hand, step 410 determines that the measured pressure value $P_1$ is within the predefined tolerance band, the method returns to step 405 and waits for the next sampled pressure value. On the other hand, if step 410 determines that the measured pressure value $P_1$ is not within that the predefined tolerance band about the setpoint value, the method continues to step 415 by determining a rate of change of the pressure, to correct for the difference. In particular, in the illustrated embodiment, step 415 calculates a value for the speed N for the piston 36 to be driven by stepper motor 44, where N is the number of steps of the stepper motor per second, using the equation:

$$N = \frac{((P_1 - S)^2 * S)}{(R)} \quad (1)$$

Where: N is the number of steps
$P_1$ is the actual measured pressure
S is the set point or desired pressure
* is the multiplier operation
R is a predetermined regulation constant A regulation constant is used to smooth the regulation of pressure and prevent oscillation of the system.

In one embodiment, the value of speed N is limited by a predefined, maximum threshold value T for the number of steps N per second for the stepper motor 44. In one embodiment, T is 2000 steps per second. Limiting the speed in this way ensures that the reaction time is always delayed, thereby ensuring that the pressure does not overshoot or undershoot the tolerance band. Thus, if step 415 calculates a value N that exceeds the threshold value, the threshold value T is instead used for the motor speed N.

Next, at step 420, the method determines if the sampled pressure $P_1$ is greater than the setpoint value, in order to determine the direction of movement of the piston. If step 420 determines that the pressure $P_1$ is greater than the setpoint, the method continues with step 425, by sending a signal to stepper motor controller and driver 48 to control the stepper motor 44 to drive the piston 36 at speed N backwards in the cylindrical bore 34 to increase the volume of, and thus reduce the pressure in, the closed volume pressure system, and thus reduce pressure in the inflatable cuff 26. Alternatively, if step 420 determines that the pressure $P_1$ is less than the setpoint, the method continues with step 430, by sending a signal to stepper motor controller and driver 48 to control the stepper motor 44 to drive the piston at speed N forwards in the cylindrical bore 34 to reduce the volume of, and thus increase the pressure in, the closed volume pressure system, and thus increase pressure in the inflatable cuff 26.

Following either step 425 or 430, the method returns to step 405 and waits for the next sampled pressure value. Typically, pressure values for $P_1$ are periodically received at regular time periods, for example every 0.5 seconds. It will be appreciated that in other embodiments, other values for the time period between samples may be used, and consequent changes in the equation for calculating the speed of the piston, may be used. However, sampling the pressure every 0.5 seconds in combination with the calculation of the rate of change of volume/pressure using the above equation (1) has been found to produce good results, since the speed N is recalculated after only half the previously calculated number of steps to correct the pressure have been completed.

Thus, the method of this embodiment of the present invention periodically samples the pressure of the system and responds to changes with a reaction speed that is dependent upon the difference between the measured pressure and the desired pressure (i.e. setpoint), subject to a predefined, maximum threshold value. Thus, the regulation of the pressure, in the closed volume system, is continually varied by changing the piston speed, which effects the change in pressure. The method drives the piston 36 at high speed when the difference between actual and set-point pressure is high and will slow down the piston speed once the measured pressure gets close to the set-point pressure. Thus, a smoother regulation of pressure is achieved by controlling the rate of change in pressure in response to detected pressure deviations. By making gradual changes to the pressure, to correct for deviation from the desired pressure, the problems associated with making instantaneous changes may be obviated.

Figure 5A:
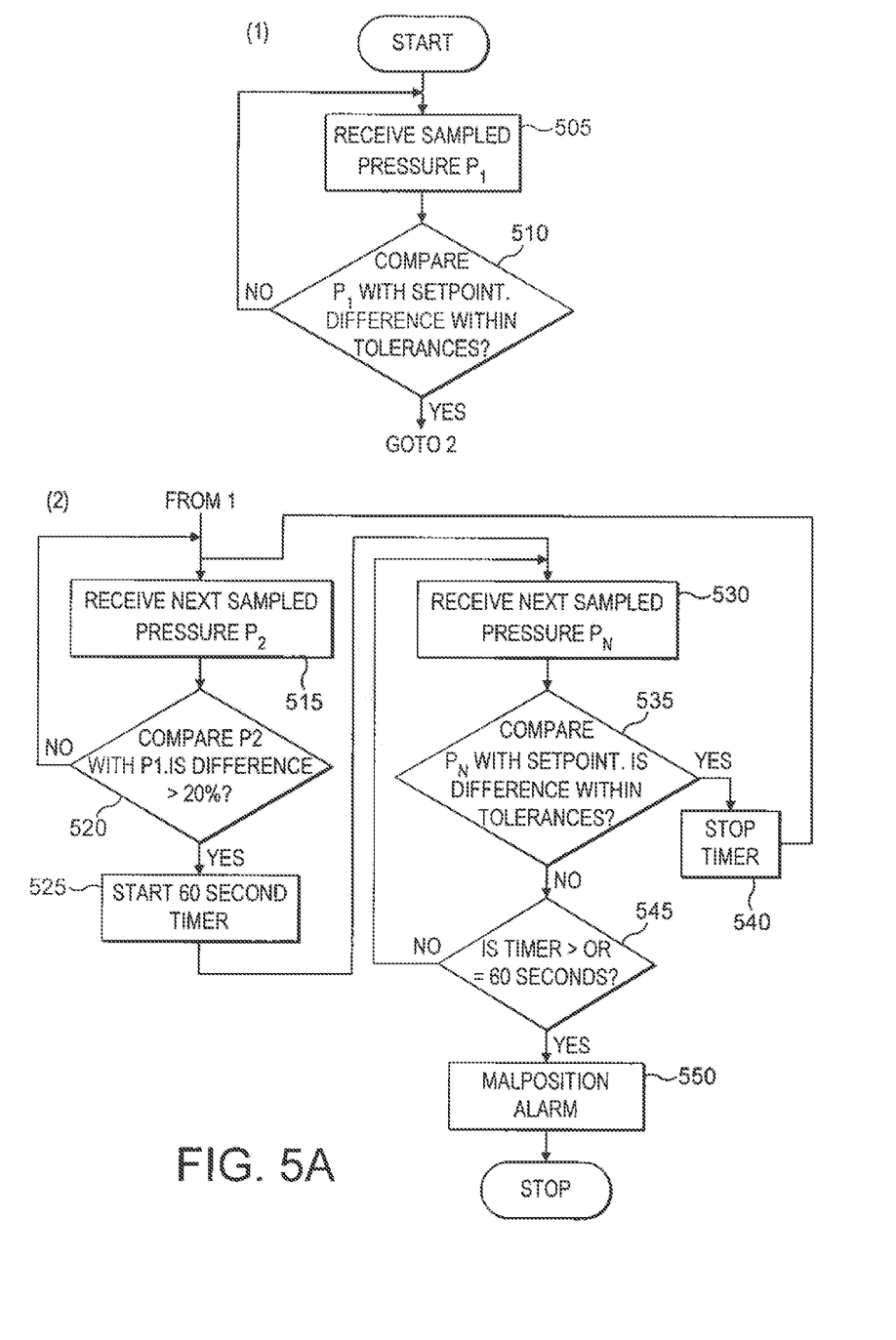
FIG. 5A and FIG. 5B are a flow diagrams, illustrating the method steps performed for detecting a positional change of an airway device, in accordance with a second embodiment of the present invention.

FIG. 5A is a flow diagram illustrating the steps performed by processor 50 implementing a method for detecting a change in position of an inflated airway device 14 in accordance with another embodiment of the present invention. As explained above, a change in position of an airway device, such as an endotracheal tube, may arise during medical or surgical procedures. Such changes may lead to extubation, whereby the endotracheal tube cuff is unintentionally withdrawn into the patient's larynx or upper airway. The laryngeal volume is normally considerably greater than that of the trachea, and it is therefore possible to detect such hidden extubation by monitoring for a substantial drop in pressure, typically a drop in pressure of 20% or more. The method starts after first establishing a pressure $P_1$ of the inflatable cuff of the airway device 14 within a predefined tolerance band, centred about a preselected set point pressure value, in accordance with a conventional System Start-Up procedure. As the skilled person will appreciate, the setpoint is chosen from a number of possible midline pressure values which are typically used for different patients such as children, male and female adults. In this embodiment, cuff pressures values of 20, 30, 40 and 50 mmHg may be selected by the operator, although the apparatus may provide for other suitable pressure values to be selected.

Accordingly, at step 505, the method receives a measured pressure value from one of the first and second pressure sensors PS1, PS2 of apparatus 10 indicating the pressure $P_1$ of the inflatable cuff. At step 510, the method compares the measured pressure value $P_1$ with the selected setpoint value, to determine a difference, and considers whether the difference is within the predefined tolerance band. If step 510 determines that the measured pressure value $P_1$ is not within the predefined tolerance, the method returns to step 505. Alternatively, if step 510 determines that the measured pressure value $P_1$ is within that the predefined tolerance band, the method continues to the second stage at step 515.

At step 515, the method receives a further measured pressure value $P_2$ from one of the first and second pressure sensors of apparatus 10. Step 520, compares the further measured pressure value $P_2$ with the previous measured pressure value $P_1$ to determine a difference, and considers whether the difference is greater than a predetermined amount, in this case 20% of the previous measured pressure value $P_1$. It will be appreciated that the predetermined amount might equally be a different proportion of the previous measured value, for example in the range of 15% to 30%, a corresponding proportion of the setpoint value, or a fixed, predetermined pressure difference (e.g. 10 to 25 mmHg).

If step 520 determines that the difference is not greater than the 20%, the method returns to step 515. Alternatively, if step 520 determines that the difference is greater than 20% of the previous measured pressure value $P_1$ (or alternatively the setpoint value or fixed pressure difference), the method continues with step 525.

As the skilled person will appreciate, instead of comparing the measured pressure value with the previous pressure value to determine a difference, and then comparing the difference with a threshold, it would be equally possible for step 520 to compare the measured pressure value $P_2$ with a predetermined minimum pressure value to achieve the same result. For example, the minimum pressure value could be 80% of the previous of predetermined pressure value $P_1$. In that case, step 520 would compare $P_2$ with 80% of $P_1$ and determine if $P_2$ is less than or equal to 80% of $P_1$, and if so proceed with step 525.

At step 525, the method starts a timer. In this embodiment, the timer is set for 60 seconds, but it will be appreciated that in the embodiments, alternative durations for the timer may be used, for example in the range 15 seconds to 2 minutes.

Whilst the timer, started in step 525, is running, the method continues with step 530 by receiving a next measured pressure value $P_N$. At step 535, the method compares the next measured pressure value $P_N$ with the setpoint value to determine a difference, and considers whether the difference is within the predefined tolerance band. If step 535 determines that the measured pressure value $P_N$ is within the predefined tolerance band, centred about the setpoint value, the method continues to step 540 which stops the timer. The method then returns to step 515. Alternatively, if step 535 determines that the measured pressure value $P_N$ is not within the predefined tolerance band, the method continues with step 545 by considering whether the timer has expired. If the timer has not expired, the method returns to step 530 by receiving a next measured pressure value $P_N$ (as mentioned above, typically, pressure values are sampled at periodic time intervals, for example every 0.5 seconds). Alternatively, if the timer has expired, the method continues to step 550 by determining a significant change in position of the airway device, and activating a "Malposition Alarm".

The step 550 of activating a Malposition Alarm may be to provide one or more signals to sound an audible alarm and/or a visual alarm on user interface 52 formed on the housing of the apparatus 10.

Following step 550, the method stops, but may be repeated once the airway device 14 has been repositioned and the apparatus 10 reset.

It will be appreciated that in some embodiments, the method of FIG. 5A may be used in conjunction with a method that automatically activates an alarm, if the measured pressure drops by a substantial amount, such as 50% or more of the desired pressure value. Such a method is described in connection with FIG. 7 below.

Figure 5B:
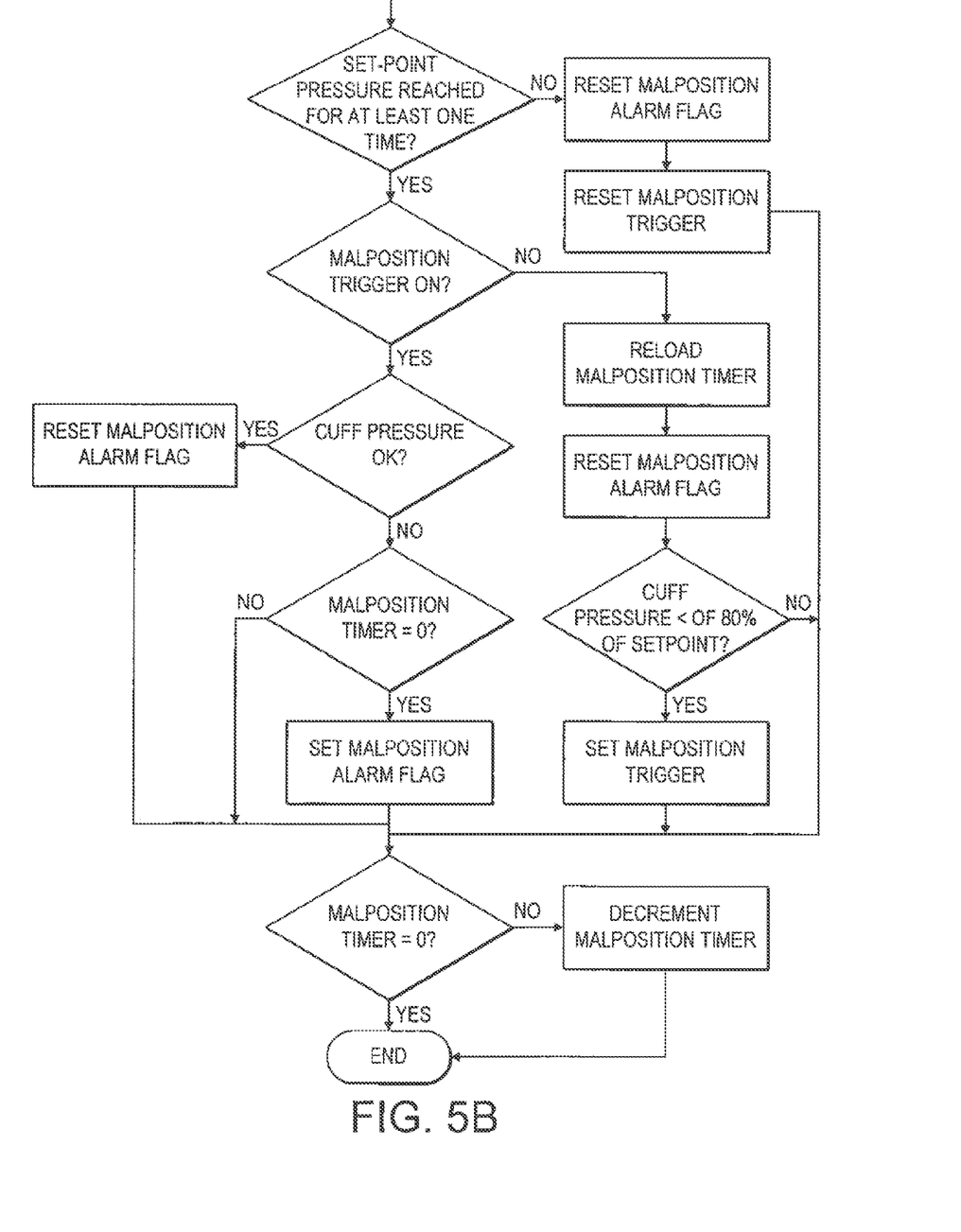

FIG. 5B is a flow diagram illustrating an algorithm implemented by the method of FIG. 5A.

Figure 6A:
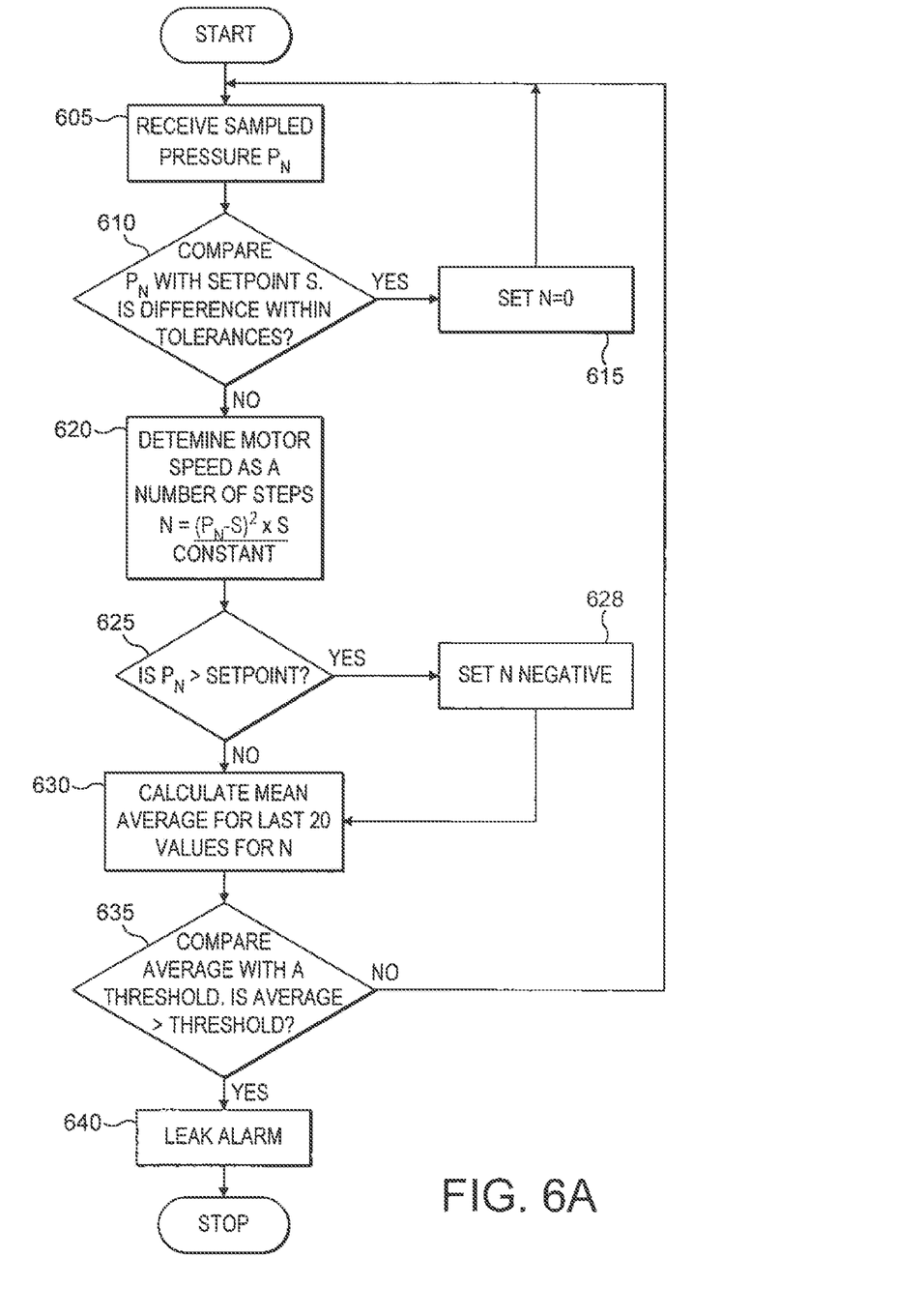
FIG. 6A and FIG. 6B are flow diagrams, illustrating the method steps performed for detecting a leak in the pressure system of an airway device, in accordance with a third embodiment of the present invention.

FIG. 6 is a flow diagram illustrating the steps performed by processor 50 implementing a first method for detecting a leak of fluid, typically air, from a closed volume pressure system of an inflatable airway device, in accordance with another embodiment of the present invention.

A leak of air or other fluid used to pressurise an inflatable seal of an airway device can adversely affect the proper functioning of the pressure monitoring and control system 10. It is therefore important to monitor for and detect leaks, to enable these to be manually corrected, wherever possible. In accordance with the present invention, this can be achieved by monitoring the pressure of the inflatable seal.

During use of an airway device, it is possible that a leak may be present in the airway device. Such a leak may be caused by perforation during surgery, or may be a slow leak from connections in the pressure system. According to the present invention, if a leak occurs whilst the airway device in use, it can be detected by calculating a statistical average of a number of values, that are each dependent on a corresponding number of previously received pressure values, and comparing it with a threshold statistical average. For example, the value may be a calculated rate of change of volume or pressure, as determined in accordance with the first aspect of the present invention. If the average is above a threshold, this indicates significant changes have been necessary over an immediately preceding time interval, to increase pressure to the desired pressure, thus signifying a possible leak of fluid.

This is implemented in the method of FIG. 6, which is performed during and/or after the conventional System Set-up procedure of the apparatus 10. In particular, at step 605, the method receives a measured pressure value $P_N$ from one of the first and second pressure sensors PS1, PS2 of apparatus 10 corresponding to a pressure of the inflatable cuff 26. Step 610 the method compares the measured pressure value $P_N$ with the selected setpoint value, to determine a difference, and considers whether the difference is within a predefined tolerance band. If step 610 determines that the measured pressure value $P_N$ is within the predefined tolerance band centred about the setpoint value, the method sets a value N to zero at step 615. The method then returns to step 605, and receives the next sampled pressure value after a predefined sampling period. Alternatively, if step 610 determines that the measured pressure value $P_N$ is not within the predefined tolerance band, the method continues with step 615.

At step 620, the method determines a rate of change of volume, and thus pressure, to correct for the difference. In particular, in the illustrated embodiment, step 615 calculates a value for the speed for the piston 36 to be driven by stepper motor 44 corresponding to the number of steps N of the stepper motor per second, e.g. by using equation (1) above.

At step 625, the method determines whether the measured pressure value $P_N$ is greater that the setpoint or desired pressure value. If the measured pressure value $P_N$ is greater than the setpoint or desired pressure value, then the setpoint pressure has been surpassed, and there can be no leak, and in some embodiments, the method may then stop. However, in the present embodiment, if step 625 determines the measured pressure value $P_N$ is greater than the setpoint or desired pressure value, the method sets the value N as negative at step 628. Otherwise, if the measured pressure value $P_N$ is less that the setpoint pressure value, the value for N is positive and the method continues with step 630.

Step 630 calculates a statistical average for the rate of change of volume/pressure (e.g. calculated as a mean average) for a previous predetermined number of samples, for example, the previous 20 samples (i.e. the value of N calculated for $P_N$ and the value of N calculated for previous 19 samples pressure values). At step 635, the method compares the average calculated in step 630 with a predefined threshold. The threshold is a minimum average value that is indicative of a ineffective operation of pressure regulation in response to pressure reductions arising during normal usage in a patient. In a preferred embodiment, the threshold is 400, which represents a normal average value for N over 10 seconds of a breathing cycle (N including inflation (positive), deflation (negative) and static steps). The value of the threshold may be adjustable by the operator, and may be set low, to detect minor leaks, or high to detect only more substantial leaks.

If step 635 determines that the average value is below the threshold, the method returns to step 605. Alternatively, if step 635 determines that the average value is above the threshold, the method continues with step 640.

Step 640 indicates that there is a leak in the closed volume pressure system of the airway device, and thereby activates a "Leak Alarm".

The step 640 of activating a Leak Alarm may be to provide one or more signals to sound an audible alarm and/or a visual alarm on the user interface 52 on the housing of the apparatus 10. These alarms signal to the operator to check the connections in the closed volume pressure system, to try to remedy the loss of air.

Following step 640, the method stops. The method may be repeated once the apparatus 10 has been reset.

It will be appreciated that whilst the method of FIG. 6A determines an average for the calculated value N, and compares it with a threshold, in other embodiments other values may be used such as the average measured pressure value. By using an average value, the method takes account of normal pressure fluctuations associated with the breathing or ventilation cycle.

Figure 6B:
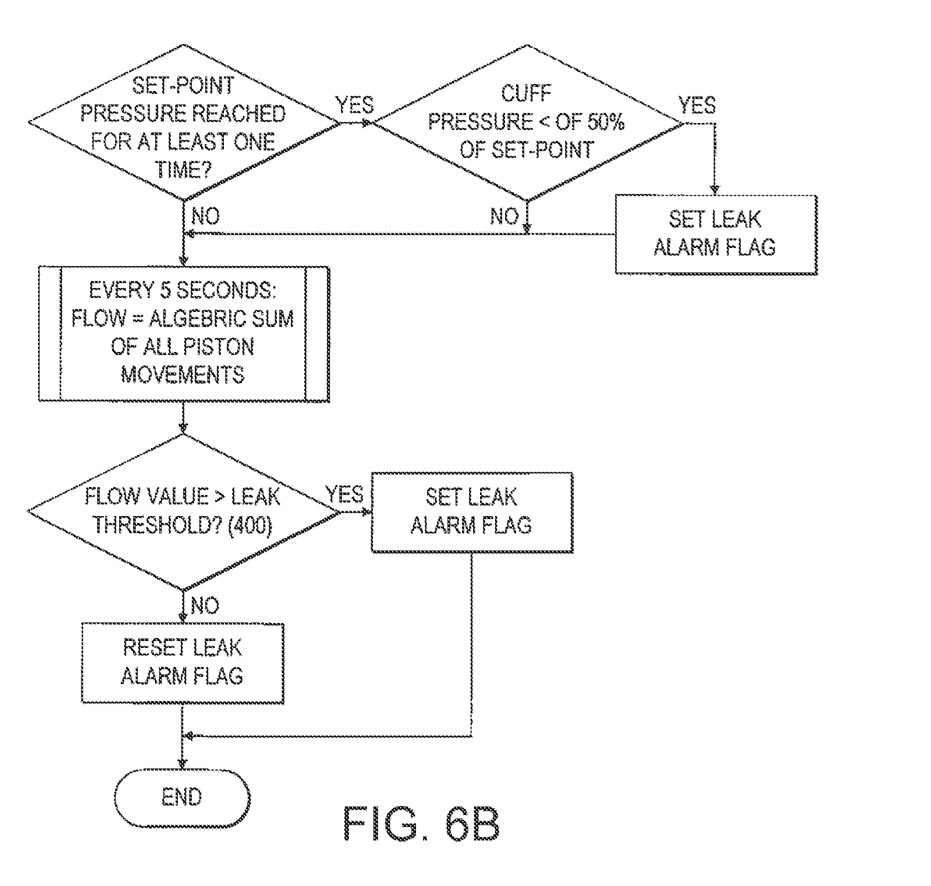

FIG. 6B is a flow diagram illustrating an algorithm implemented by the method of FIG. 6A.

Figure 7:
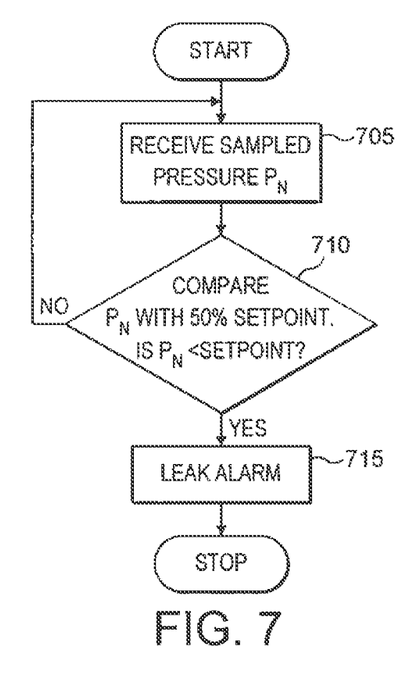
FIG. 7 is a flow diagram, illustrating the method steps performed for detecting a leak in the pressure system of an airway device, in accordance with a fourth embodiment of the present invention.

FIG. 7 is a flow diagram illustrating the steps performed by processor 50 implementing another method for detecting a leak of fluid, typically air, from an inflatable airway device, in accordance with another embodiment of the present invention.

As explained previously, during use of the apparatus of the present invention, it is possible that a leak may be caused in the airway device, for example due to perforation during surgery. According to the present invention, if a leak occurs whilst the airway device in use, it can be detected by monitoring for a sudden drop in the pressure value for the inflatable airway device below a minimum pressure. Typically, the minimum pressure value is 50% of the desired or setpoint pressure for the airway device.

This is implemented in the method of FIG. 7, which is performed after the Setup procedure of the apparatus 10, i.e. when the apparatus is in normal use.

At step 705, the method receives a measured pressure value $P_N$ from one of the first and second pressure sensors PS1, PS2 of apparatus 10 corresponding to a pressure $P_N$ of the inflatable cuff 26.

At step 710, the received measured pressure value $P_N$ is compared with a predefined pressure value, in this embodiment corresponding to 50% of the selected setpoint value, to determine if $P_N$ is less than 50% of the setpoint value S. If step 710 determines that the measured pressure value is more than 50% of the setpoint value, the method returns to step 705. Alternatively, if step 710 determines that the measured pressure value is less than 50% of the setpoint value, the method continues to step 715 by indicating a leak in the air inflation system of the airway device, and thereby activating a "Leak Alarm".

The step 715 of activating a Leak Alarm may be to provide one or more signals to sound an audible alarm and/or a visual alarm on the user interface 52 of the housing of the apparatus 10. This may be the same or a different alarm to that of step 635 of FIG. 6. This signals to the operator to check the connections in the closed volume pressure system, to try to remedy the loss of air.

Following step 715, the method stops. The method may be repeated once the apparatus 10 has been reset.

Figure 8:
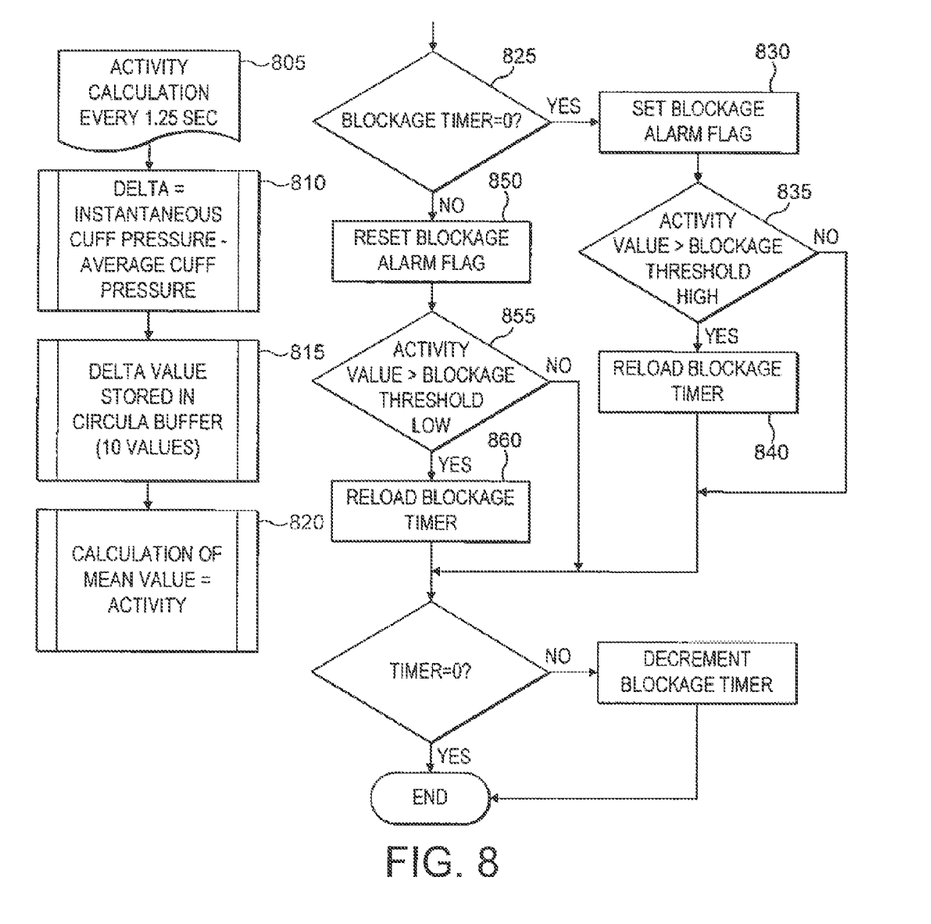
FIG. 8 is a flow diagram, illustrating the method steps performed for detecting a blockage in the pressure system of the airway device, in accordance with a fifth embodiment of the present invention.

FIG. 8 is a flow diagram illustrating the steps performed by processor 50 implementing a method for detecting a blockage in the pressure system of an inflatable airway device, in accordance with yet another embodiment of the present invention.

As discussed above, solid material can be introduced into a closed volume pressure system of an airway device 14 attached to a pressure monitoring and control apparatus 10 in certain circumstances. This can lead to a blockage, typically in the inflation line 12, adversely affecting the proper functioning of the monitoring and control apparatus 10. When a blockage occurs, the pressure becomes substantially static, and normal cyclic changes of pressure, associated with ventilation, are not detected. The present invention detects a blockage in the pressure system of an airway device if the average value of deviations in pressure from a desired value (herein termed "activity"), is below a threshold for a predetermined time period. The threshold is typically less that an average of pressure deviations over the predetermined time period that would be expected to arise as a result of the breathing cycle.

The method periodically calculates a value for activity, typically every 1.25 seconds, as follows. At step 805 an instantaneous pressure value $P_N$ is received from one of the first and second pressure sensors PS1, PS2 of apparatus 10 indicating the pressure of the inflatable cuff 26. At step 810 the difference between the measured pressure value and a predefined (or precalculated) average pressure value is determined and at step 815 the difference is stored in a circular buffer, which stores the current and a predetermined number of previously calculated pressure differences (in this case 10 values in total). Step 820 calculates the Activity value as the mean average of the values stored in the circular buffer.

This mean average is an indicator of the activity which normally arises from the breathing cycle. In particular, during normal operation, cyclic positive and negative pressure fluctuations occur around the set-point value due to either the patient spontaneously breathing or the mechanical ventilation applied. During each cycle, the difference in pressure from the setpoint may vary from 0.5 up to 3-5 cm $H_2O$ (1 mmHg=1.395 mmH2O).

The method uses a timer to determine whether the activity levels are below a threshold for a significant time period indicative or a blockage. Typically the timer is triggered by a lower threshold for activity (e.g. the lower threshold is 3) and runs for 3 minutes (180 seconds) although other time periods between 1 to 5 minutes are possible. It the timer expires without being reset, then a Blockage alarm is activated. However, if the activity rises above an upper threshold (e.g. 8) before the timer expires, the timer is reset or stopped.

It will be appreciated that the Blockage alarm may be to provide one or more signals to sound an audible alarm and/or a visual alarm on the user interface 52 on the housing of the apparatus 10. This signals to the operator to check for a blockage in the closed volume pressure system.

Referring again to FIG. 8, step 825 determines whether the timer has expired, and, if so, sets a Blockage alarm flag at step 830 to initiate a Blockage alarm. Following step 830, the method compares the current activity value with an upper threshold value at step 835 and determines if the activity is greater than the upper threshold. The upper threshold is a value for activity indicative of normal pressure fluctuations associated with the breathing cycle. If the activity is greater that the upper threshold, then there is no blockage; then the activity is sufficient to demonstrate that air is passing through the inflation line 12. In one embodiment, the value of the upper threshold is 8. Accordingly, if step 835 determines the activity is greater than the upper threshold, step 840 continues by reloading the timer.

On the other hand, if step 825 determines that the timer has not expired, step 850 resets the blockage alarm flag and step 855 determines whether the current activity is greater than a lower threshold. In one embodiment, the lower threshold is 3. If step 855 determines that the activity value is above the lower threshold, then the activity is below normal activity levels indicated by upper threshold and step 860 continues by reloading the Blockage timer.

The described device and its method of use acts as a controller of the cuff pressure of an airway device such as an endotracheal tube. A device incorporating aspects of the present invention will perform one or more of the following functions:
a) perform pressure corrections, at a controlled rate, in response to periodically measured pressure changes that do not arise from normal respiratory movement so as to maintain the pressure within a desirable range (preventing overshoot and undershoot);
b) monitor for leaks in the pressure system and raise an alarm if a leak is detected;
c) monitor for deviations from the correct position of the airway device that results in partial or full extubation and raise an alarm if a malposition is detected;
d) monitor for blockage in the pressure system and raise an alarm is a blockage is detected.

These functions may be included in combination with existing functions of prior art devices, such as that disclosed in WO-A-99/33508.

The device is controlled by a microprocessor 50 which performs all tasks including, but not limited to, diagnostic checks, motor and valve operation and control, and pressure measurement. Typically, the device includes a user interface 52 including a graphic display for pressure indications and alarms, and control unit with an interface providing for outputting data for advanced monitoring and control thus permitting data evaluation with different commercial software packages.

In its normal regulation mode, system pressure sampling is at every 0.5 seconds, which provides sufficient time between samples to perform evaluation against set-point pressure, and issue control signals, in the form of a train of pulses, to the motor controller to drive the piston to displace air in the closed volume system, and thus change the pressure to substantially setpoint pressure.

A system incorporating several or all the aspects of the present invention, discussed above, provides considerable assistance to the anaesthetist during a surgical procedure on a patient. In particular, such a system provides several concurrently operative algorithms to process, in real time or in close to real time, the operating status of the airway device, and audibly and/or visually alerts the anaesthetist of any adverse changes.

As the skilled person will appreciate, various changes and modifications can be made to the described embodiments. It is intended to include all such variations, modifications and equivalents which fall within the scope of the invention, as defined in the accompanying claims.

The invention claimed is:

1. A method for detecting a change in position of an airway device with an inflatable seal having a first measured pressure value within a predefined tolerance band centered about a preselected set point pressure value, the method comprising:
   receiving a second measured pressure value indicative of the pressure of the inflatable seal and comparing the second measured pressure value to the first measured pressure value to determine a first difference;
   determining whether the first difference is greater than a predetermined amount;
   starting a timer for a predetermined time period if the difference is greater than the predetermined amount;
   while the timer is running, receiving a third pressure value indicative of the pressure of the inflatable seal and comparing the third pressure value with the preselected set point pressure value to determine a second difference;
   determining whether the second difference is within the predefined tolerance band;
   indicating a detected change in position of the airway device if the predetermined time period of the timer has expired and the second difference is outside the predefined tolerance band.

2. The method of claim 1, further comprising the step of receiving further measured pressure values indicative of the pressure of the inflatable seal if the first difference is not greater than the predetermined amount.

3. The method of claim 1, wherein the predetermined amount is selected from the group consisting of a proportion of the first measured pressure value, a proportion of the set point pressure value and a fixed, predetermined pressure difference.

4. The method of claim 3, wherein the proportion of the first measured pressure value and the proportion of the set point pressure value are in the range of 15% to 30%.

5. The method of claim 1, further comprising the step of receiving further measured pressure values indicative of the pressure of the inflatable seal if the timer is still running.

6. The method of claim 5, further comprising the step of receiving the further measured pressure values indicative of the pressure of the inflatable seal if the second difference is within the predefined tolerance band.

7. A method for detecting a change in position of an airway device with an inflatable seal having a first measured pressure value within a predefined tolerance band centered about a preselected set point pressure value, the method comprising:
   receiving a second measured pressure value indicative of the pressure of the inflatable seal and comparing the second measured pressure value to a predetermined minimum pressure value to determine whether the second measured pressure value is less than or equal to the predetermined minimum pressure value;
   starting a timer for a predetermined time period if the second measured pressure value is less than or equal to the predetermined minimum pressure value;
   while the timer is running, receiving a third pressure value indicative of the pressure of the inflatable seal and comparing the third pressure value with the preselected set point pressure value to determine a difference;
   determining whether the difference is within the predefined tolerance band;
   indicating a detected change in position of the airway device if the predetermined time period of the timer has expired and the difference is outside the predefined tolerance band.

8. The method of claim 7, wherein the predetermined minimum pressure value is selected from the group consisting of a proportion of the first measured pressure value, a proportion of the set point pressure value and a fixed, predetermined pressure amount.

9. The method of claim 7, further comprising the step of receiving further measured pressure values indicative of the pressure of the inflatable seal if the second measured pressure value is greater than the predetermined minimum pressure value and the timer is still running.

10. The method of claim 7, further comprising the steps of receiving further measured pressure values indicative of the pressure of the inflatable seal and stopping the timer if the difference is within the predefined tolerance band.

* * * * *